(12) United States Patent
Stevens

(10) Patent No.: US 11,371,103 B2
(45) Date of Patent: Jun. 28, 2022

(54) ENERGY RECAPTURING APPARATUS

(71) Applicant: Alternative Sustainability IP LLC, Fleming Island, FL (US)

(72) Inventor: John A. Stevens, New York, NY (US)

(73) Assignee: Alternative Sustainability IP LLC, Fleming island, FL (US)

( * ) Notice: Subject to any disclaimer, the term of this patent is extended or adjusted under 35 U.S.C. 154(b) by 0 days.

(21) Appl. No.: 17/491,359

(22) Filed: Sep. 30, 2021

(65) Prior Publication Data

US 2022/0042451 A1 Feb. 10, 2022

Related U.S. Application Data

(60) Provisional application No. 63/198,207, filed on Oct. 2, 2020.

(51) Int. Cl.
| | |
|---|---|
| *F03D 9/00* | (2016.01) |
| *H02P 9/04* | (2006.01) |
| *C12Q 1/689* | (2018.01) |
| *F03G 7/00* | (2006.01) |
| *F02C 1/02* | (2006.01) |
| *F24F 12/00* | (2006.01) |

(52) U.S. Cl.
CPC ............... *C12Q 1/689* (2013.01); *F02C 1/02* (2013.01); *F03G 7/0252* (2021.08); *F24F 12/00* (2013.01); *C12Q 2600/158* (2013.01); *F05B 2220/604* (2013.01); *F05D 2220/32* (2013.01); *F05D 2220/74* (2013.01); *F05D 2220/76* (2013.01)

(58) Field of Classification Search
CPC .......... F24F 12/00; F03G 7/0252; F03B 3/04; F03B 11/02; H02K 5/22; H02K 5/26; H02K 2205/09; H02K 2205/12; F05D 2220/20; F05D 2220/60; F05D 2220/62; F05B 2220/20; F05B 2220/60; F05B 2220/602
See application file for complete search history.

(56) References Cited

U.S. PATENT DOCUMENTS

| | | | | |
|---|---|---|---|---|
| 3,998,057 | A * | 12/1976 | Haferkamp | ............. G21D 5/06 376/393 |
| 4,006,672 | A * | 2/1977 | Matsuyoshi | ............ F24F 13/20 454/343 |
| 5,148,767 | A * | 9/1992 | Torchio | .................. A01K 1/035 119/484 |
| 5,512,788 | A | 4/1996 | Berenda et al. | |

(Continued)

FOREIGN PATENT DOCUMENTS

| | | |
|---|---|---|
| DE | 29521926 U | 9/1998 |
| JP | 2008002322 A1 | 1/2008 |

(Continued)

*Primary Examiner* — Tulsidas C Patel
*Assistant Examiner* — Thomas K Quigley
(74) *Attorney, Agent, or Firm* — MG Miller Intellectual Property Law LLC

(57) ABSTRACT

An energy recapturing apparatus is disclosed. The energy recapturing apparatus is housed within a frame that is configured to fit within a preexisting fluid passageway. The frame is further attached to a sliding mechanism, which enables the frame to be easily removed from the preexisting fluid passageway. Further, the frame is configured to accept at least one turbine that contains a plurality of blades. The turbine is able to convert the energy of fluid movement into electricity.

20 Claims, 6 Drawing Sheets

(56) References Cited

U.S. PATENT DOCUMENTS

| | | | | |
|---|---|---|---|---|
| 5,582,026 | A * | 12/1996 | Barto, Sr. | F24F 1/0003 62/298 |
| 6,097,104 | A | 8/2000 | Russell | |
| 6,115,250 | A * | 9/2000 | Schmitt | G06F 1/20 165/104.34 |
| 6,365,985 | B1 | 4/2002 | Cohen | |
| 7,112,893 | B1 * | 9/2006 | Villanueva | F03D 9/37 60/641.11 |
| 8,368,240 | B1 * | 2/2013 | Burkett | F03D 9/11 290/55 |
| 8,939,724 | B2 | 1/2015 | Koya et al. | |
| 9,562,517 | B1 | 2/2017 | Decady | |
| 9,661,787 | B2 * | 5/2017 | Hall | F04D 25/166 |
| 10,271,459 | B2 * | 4/2019 | Campbell | H05K 7/20727 |
| 10,418,654 | B2 * | 9/2019 | Trevisan | H01M 8/04089 |
| 2008/0188174 | A1 | 8/2008 | Aminpour et al. | |
| 2010/0117370 | A1 | 5/2010 | Phelps | |
| 2011/0215579 | A1 | 9/2011 | Barzilai et al. | |
| 2012/0280503 | A1 | 11/2012 | Mahawili | |
| 2013/0167657 | A1 * | 7/2013 | Chang | F04D 27/001 73/861.85 |
| 2013/0170518 | A1 * | 7/2013 | Chang | G01M 99/002 374/141 |
| 2014/0183871 | A1 | 7/2014 | Baptiste | |
| 2016/0091247 | A1 * | 3/2016 | DiMenichi | F26B 21/006 34/104 |
| 2016/0381836 | A1 * | 12/2016 | Hall | F04D 29/522 361/679.48 |
| 2017/0292724 | A1 * | 10/2017 | Klapishevsky | F24F 11/0001 |
| 2021/0027661 | A1 * | 1/2021 | Dixon | B01L 9/52 |
| 2022/0042451 | A1 * | 2/2022 | Stevens | F03G 7/0252 |

FOREIGN PATENT DOCUMENTS

| | | |
|---|---|---|
| KR | 101765703 B1 | 8/2017 |
| WO | 2011058396 A2 | 5/2011 |

\* cited by examiner

ENERGY RECAPTURING APPARATUS

CLAIM OF PRIORITY

This application claims priority to U.S. Provisional Patent Application No. 63/198,207, filed Oct. 2, 2020, entitled "Energy Recapturing Apparatus", the contents of which are hereby incorporated by reference in their entirety.

NOTICE OF COPYRIGHTS AND TRADE DRESS

A portion of the disclosure of this patent document contains material which is subject to copyright or trade dress protection. This patent document may show and/or describe matter that is or may become trade dress of the owner. The copyright and trade dress owner has no objection to the facsimile reproduction by anyone of the patent disclosure, as it appears in the Patent and Trademark Office patent files or records, but otherwise reserves all copyright and trade dress rights whatsoever.

FIELD OF THE EMBODIMENTS

The present disclosure relates generally to an apparatus for recapturing energy. More particularly, the present disclosure relates to an energy recapturing apparatus that uses a sliding frame to allow a turbine and generator to be easily retrofitted into a preexisting fluid passageway.

BACKGROUND

The earliest windmills date back to the $9^{th}$ century where they were used by Persians to grind grain and draw water. Today, the fundamentals behind the basic windmill have been extrapolated to convert the energy of the wind into electricity. Wind power has been praised as being one of the most efficient and sustainable forms of renewable energy. Consequently, the Global Wind Energy Council and Greenpeace International boast that by 2050 25 to 30% of global energy will be harvested via wind power.

The increased interest in renewable energy is directly correlated to the recent attentiveness to sustainability. As the threat of energy crisis and climate change becomes more evident, large segments of the global population have come to terms with the inarguable need to move from fossil fuels to renewable sources of energy. Accordingly, city, state, and federal, governments have taken initiative and passed a myriad of rules and regulations aimed at mitigating the burden on the environment. Specifically, many cities, including New York, have passed building regulations that dictate the manner in which a building may be constructed and/or set energy efficiency requirements. Consequently, there is a need for innovation enabling renewable energy use in urban cities. However, there are a number of distinct hurdles that are encountered when attempting to utilize wind power in urban centers.

A typical onshore wind turbine can range from 300 to 600 feet tall, with blades exceeding 100 feet in length. For most urban, and even suburban cities, a typical onshore wind turbine is physically too large to coexist with the city's buildings and inhabitants. Additionally, in the event that a typical onshore wind turbine could meet the spatial requirements for installation, there are a number of concerns including: unsightly appearance, noise pollution, and potential damages to property or life. Many residents are deterred by the physical appearance and noise created by towering wind turbines. Although such wind turbines may be beneficial to the energy needs of these cities, the "eyesore" nature of these turbines often causes property values to decline.

Furthermore, leading researchers like Dr. Nina Pierpont have determined that the sub-sonic noise created by these massive turbines can cause headaches, dizziness, and even depression. The "flicker effect" of the rotating turbines can even induce vertigo and invoke seizures in nearby residents. Although catastrophic failures are rare in wind turbines, when they do occur, such failures can launch thousands of pounds of metal through the air. Fortunately, most modern wind turbines contain rotor brakes that will stop the blades from spinning during bouts of excessive wind. However, like any mechanical safety, a rotor brake can fail causing serious damage to an urban city.

A common proposal is to move wind turbines offshore. However, there are a number of disadvantages with offshore wind power. First, offshore wind farms are very expensive to build and maintain. Second, there is empirical evidence to support that offshore wind farms kill, maim, and/or otherwise disrupt, many species of migratory birds and marine life. Third, offshore wind turbines are at an increased risk of damage due to storms, hurricanes, and high seas.

Furthermore, such massive wind turbines and wind farms are inadequate in solving one of the primary issues facing urban cities, which is that singular buildings must meet energy guidelines. Therefore, for wind turbines to be more reasonably used in urban cities, wind turbines must be scaled down in size and modified to be compatible with large urban buildings. Additionally, traditional tower-style wind turbines are ineffective in major cities where there are buildings at different heights that disrupt steady wind streams.

The majority of urban buildings have dedicated building HVAC systems, exhausts, or other airways. In fact, most cities have a number of regulations that require a building to supply fresh air throughout the structure. Thus, effectively every metropolitan building contains some form of ventilation system, often times operating constantly, providing an uninterrupted airflow.

In order to best harvest the energy of air that flows through a ventilation duct or other airway present in a building, the turbine must be situated within the airway. However, the permanent installation of a turbine within a duct can be very difficult and makes maintenance burdensome.

The invention of the present disclosure solves this problem by allowing the frame and turbine to be easily removed from the duct or airway. The invention of the present disclosure prescribes that the turbine may be mounted, either vertically of horizontally, to a sliding frame, which is then installed within an airway. Such an invention allows the turbine to harness energy from a constant airflow, which is not always the case with external wind turbines. Further, the invention of the present disclosure is housed within an airway, thus being invisible to a city's inhabitants.

In the present disclosure, where a document, act, or item of knowledge is referred to or discussed, this reference or discussion is not an admission that the document, act, item of knowledge, or any combination thereof that was known at the priority date, publicly available, known to the public, part of common general knowledge or otherwise constitutes prior art under the applicable statutory provisions; or is known to be relevant to an attempt to solve any problem with which the present disclosure is concerned.

While certain aspects of conventional technologies have been discussed to facilitate the present disclosure, no technical aspects are disclaimed. It is contemplated that the claims may encompass one or more of the conventional technical aspects discussed herein.

SUMMARY

The present disclosure provides for an energy recapturing apparatus for use with a preexisting fluid passageway. Preferably, the energy recapturing apparatus will feature a frame having a left side, a right side, a top side, and a bottom side, having a front end and a rear end, the frame sized to be fixed within a cross section of the fluid passageway, at least one turbine having a front end and a back end, and a sliding mechanism disposed on an exterior of the frame, having an extended mode and a non-extended mode. In some embodiments the at least one turbine comprises a mounting mechanism for attachment to the frame, the frame and the at least one turbine are oriented such that air passing through the cross section will also pass though the energy recapturing apparatus, the sliding mechanism is configured to support the frame and at least one turbine integrated therein, the sliding mechanism is further configured to enable the frame to be situated within the fluid passageway when the sliding mechanism in the non-extended mode, and the frame and turbine are configured to be removably attached to the fluid passageway when the sliding mechanism is in the extended mode.

In other embodiments the energy recapturing apparatus further comprises at least one turbine collar, each turbine collar having a first end with a first size, the first size being defined by a first length and a first width, a second end with a second size, the second size being defined by a second length and a second width, and at least one wall extending therebetween. Optionally, the first size may be sized to a cross section of the at least one turbine and the first end is in fluid communication with the at least one turbine.

In a preferred embodiment the at least one turbine is a plurality of turbines and wherein the first size is sized to a combined cross section of the plurality of turbines and the first end is in fluid communication with the plurality of turbines. Additionally, the at least one turbine may be at least two turbines, wherein the first width is sized to a length of a side of a turbine and the first length is sized to a combined length of a side of each of the at least two turbines, and wherein the first end is in fluid communication with the at least two turbines.

In some embodiments, the at least one turbine is a plurality of turbines, preferably the at least one turbine collar is a plurality of turbine collars, and preferably at least one of the plurality of turbines is in fluid communication with at least one of the plurality of turbine collars.

In some embodiments, the first width of each of the plurality of turbine collars is sized to a length of a side of a turbine and the first length of each of the plurality of turbine collars is sized to a combined length of a side of each of at least two turbines of the plurality of turbines. In some embodiments, the first end of each of the plurality of turbine collars is in fluid communication with at least two turbines of the plurality of turbines.

In some embodiments, the second size is defined by a cross section of the fluid passageway. In some embodiments, the combined second width and combined second length of the plurality of turbine collars is sized to a cross section of the fluid passageway. In a preferable embodiment, the second size is larger than the first size.

In some embodiments, the fluid passageway is a return air duct. In other embodiments, the fluid passageway is a building air intake. In still other embodiments, the fluid passageway is a branch line duct. In some embodiments, the fluid passageway is a return air duct. In some embodiments, the fluid passageway is a building air intake.

In some embodiments, the energy recapturing apparatus generates at least 1000 Watts of energy, preferably at least 1500 Watts of energy, more preferably at least 3000 Watts of energy. In some embodiments, the energy recapturing apparatus generates between 500 and 10,000 Watts of energy.

BRIEF DESCRIPTION OF THE PREFERRED EMBODIMENTS

In the drawings, like elements are depicted by like reference numerals. The drawings are briefly described as follows.

Figure 1:
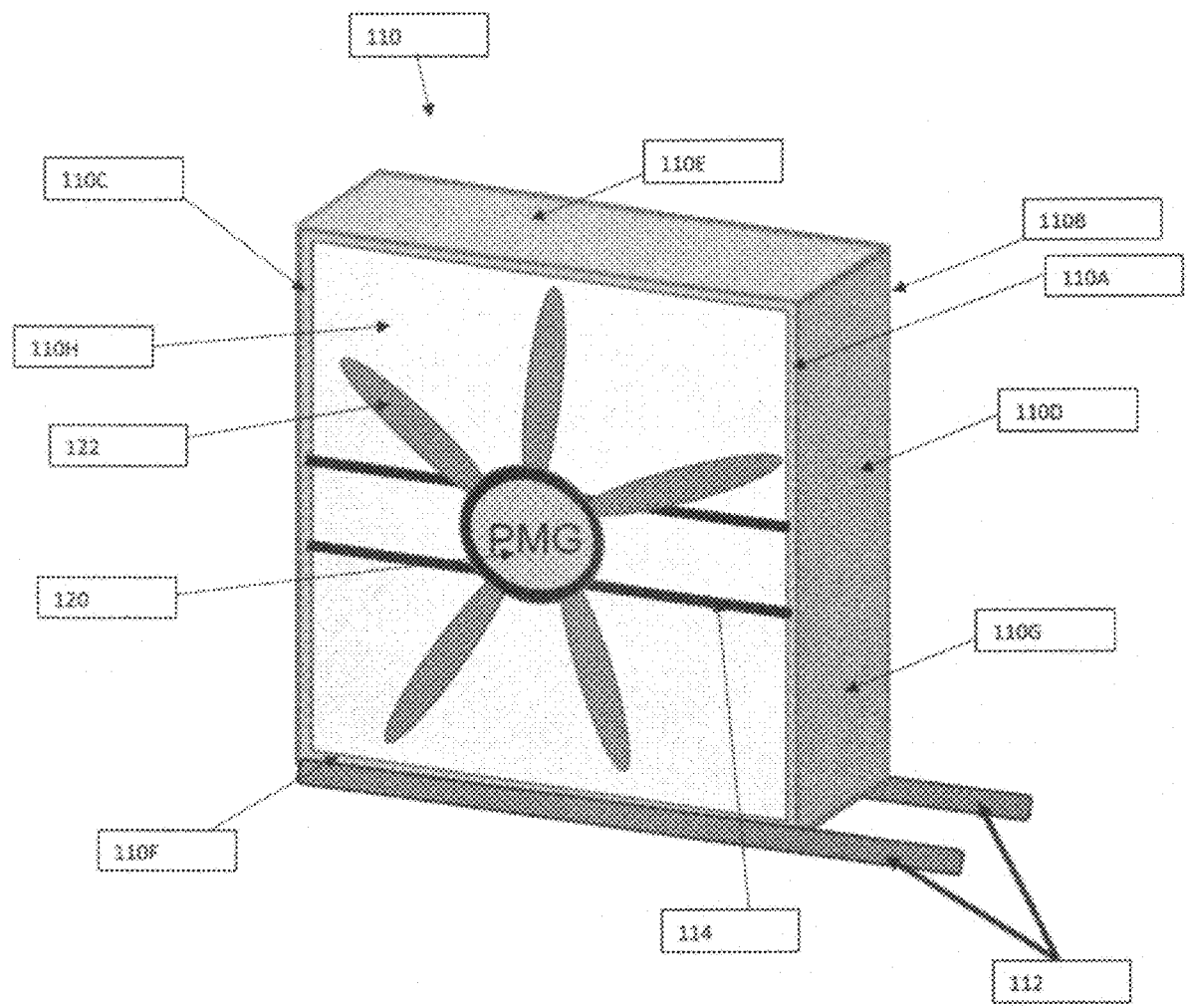
FIG. 1 is a front perspective viewing, showing an example embodiment of the energy recapturing apparatus according to the present disclosure.

The present disclosure now will be described more fully hereinafter with reference to the accompanying drawings, which show various example embodiments. However, the present disclosure may be embodied in many different forms and should not be construed as limited to the example embodiments set forth herein. Rather, these example embodiments are provided so that the present disclosure is thorough, complete, and fully conveys the scope of the present disclosure to those skilled in the art. In fact, it will be apparent to those skilled in the art that various modifications and variations can be made in the present invention without departing from the scope or spirit of the invention.

DETAILED DESCRIPTION OF THE PREFERRED EMBODIMENTS

The preferred embodiments of the present invention will now be described with reference to the drawings. Identical elements in the various figures are identified with the same reference numerals.

Reference will now be made in detail to each embodiment of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto.

The present disclosure, with reference to FIG. 1, provides an energy recapturing apparatus. Here, the apparatus has a frame 110, which includes a front end 110A, a rear end 110B, a left side 110C, a right side 110D, a top side 110E, and a bottom side 110F. In preferred embodiments, the left side 110C, the right side 110D, the top side 110E, and the bottom side 110F are disposed such that a continuous sheet 110G is created. In preferred embodiments, the left side 110C, the right side 110D, the top side 110E, and the bottom side 110F are each independent components that have been connected at each of the components ends by a means of fastening well known in the art.

Figure 2:
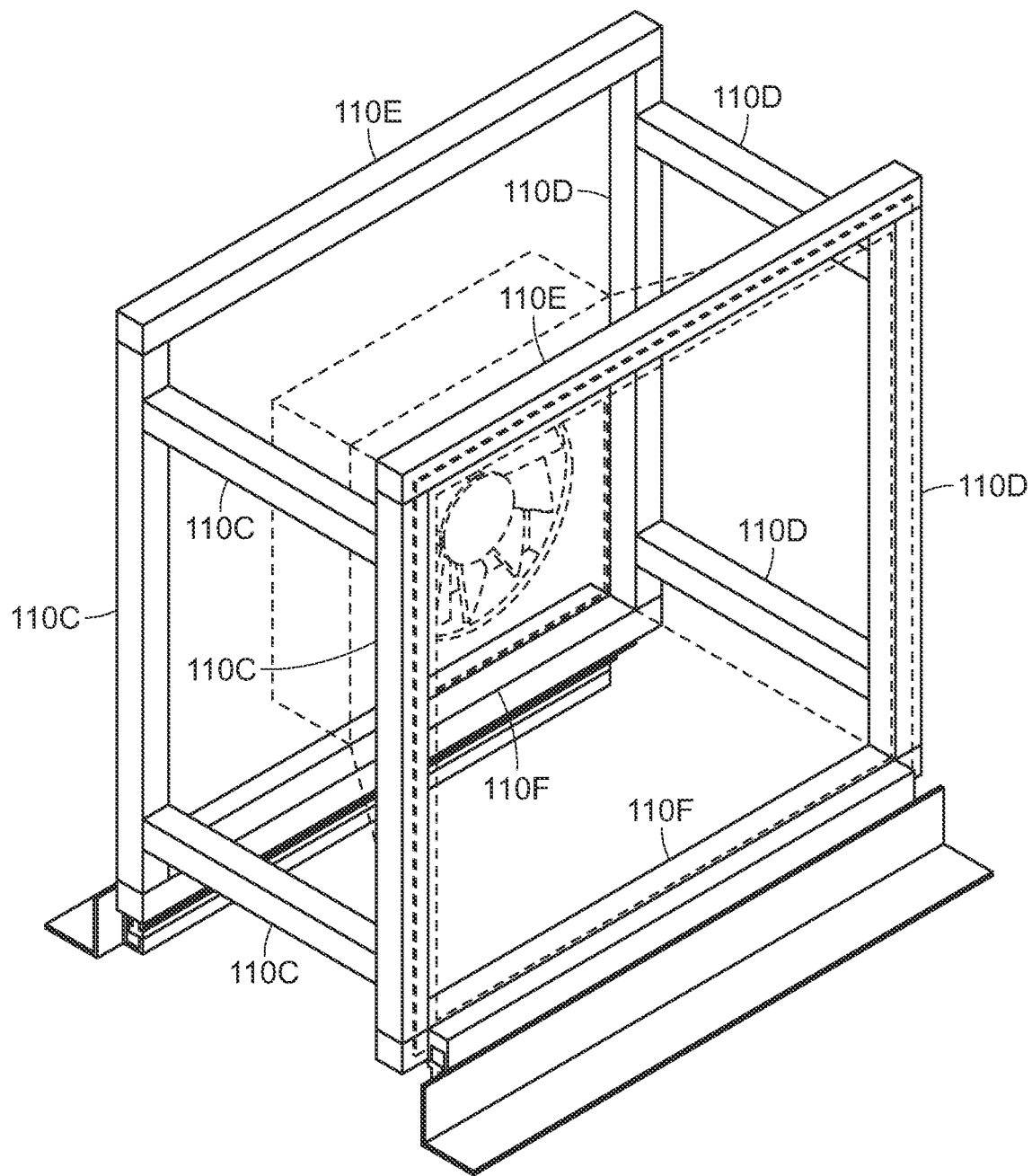
FIG. 2 is a front perspective viewing, showing an alternate example embodiment of the energy recapturing apparatus according to the present disclosure.

In preferred embodiments, with reference to FIG. 2, the left side 110C, the right side 110D, the top side 110E, and the bottom side 110F are each composed of independent, interconnected, subcomponents, such as bars or rods, that have been connected at each of the ends of the subcomponents by a means of fastening well known in the art. Connection methods include, but are not limited to, fastened by screw, bracket, adhesive, welding, or some other means of fastening.

In alternative embodiments, the frame in accordance with the present disclosure is manufactured such that the left side 110C, the right side 110D, the top side 110E, and the bottom side 110F, were not originally independent components, or consist of one, two, three, or more independent components fastened together. Instead, in this alternative embodiment, each of the one or more independent components may either be manufactured, pressed, bent, or otherwise configured to have the left side 110C, the right side 110D, the top side 110E, and the bottom side 110F, without the need for fastening. In alternative embodiments, the continuous sheet 110G is manufactured such that the left side 110C, the right side 110D, the top side 110E, and the bottom side 110F, were not originally independent components. Instead, in this alternative embodiment, the continuous sheet 110G may either be manufactured, pressed, bent, or otherwise configured to have the left side 110C, the right side 110D, the top side 110E, and the bottom side 110F, without the need for fastening.

In preferred embodiments, the continuous sheet 110G surrounds a passage 110H such that the passage 110H enables the free flow of liquid or gas. Preferably, the continuous sheet 110G is shaped as a rectangle or square. However, there are further embodiments where the continuous sheet 110G is shaped like as a circle, triangle, or other geometric shape. Preferably, each side 110C, 110D, 110E, 110F, of the continuous sheet 110G is either 9, 20, 29, 38, 47, 56, 65, or 74 inches in length and the depth of the continuous sheet 110G, as measured from the front end 110A to the rear end 110B, is 13 inches. However, in alternative embodiments, the length of each side 110C, 110D, 110E, 110F of the continuous sheet 110G and the depth of the continuous sheet 110G may be any length or depth. In the aforementioned alternative embodiments, the dimensions of the continuous sheet 110G may change as necessary to retrofit the frame 110 into the preexisting fluid passageway.

In further preferred embodiments, the frame 110 has at least one mounting bracket 114 disposed over the passage 110H. Preferably the at least one mounting bracket 114 is fastened to left side 110C and the right side 110D. However, in alternate embodiments, the at least one mounting bracket 114 is fastened to the top side 110E and the bottom side 110F. In further embodiments, the at least one mounting bracket 114 is connected to just one of the left side 110C, the right side 110D, the top side 110E, or the bottom side 110F. Alternatively, the at least one mounting bracket 114 is connected to any two of the left side 110C, the right side 110D, the top side 110E, or the bottom side 110F. Further, the at least one mounting bracket 114 may be connected to any three of the left side 110C, the right side 110D, the top side 110E, or the bottom side 110F. In another embodiment, the at least one mounting bracket 114 is connected to the left side 110C, the right side 110D, the top side 110E, and the bottom side 110F.

Preferably, the at least one mounting bracket 114 is made of metal. However, in alternate embodiments the at least one mounting bracket 114 may be composed of polymer, plastic, wood, or some other material. Preferably, the at least one mounting bracket 114 is designed to be sufficiently thin to minimize air resistance.

Figure 3:
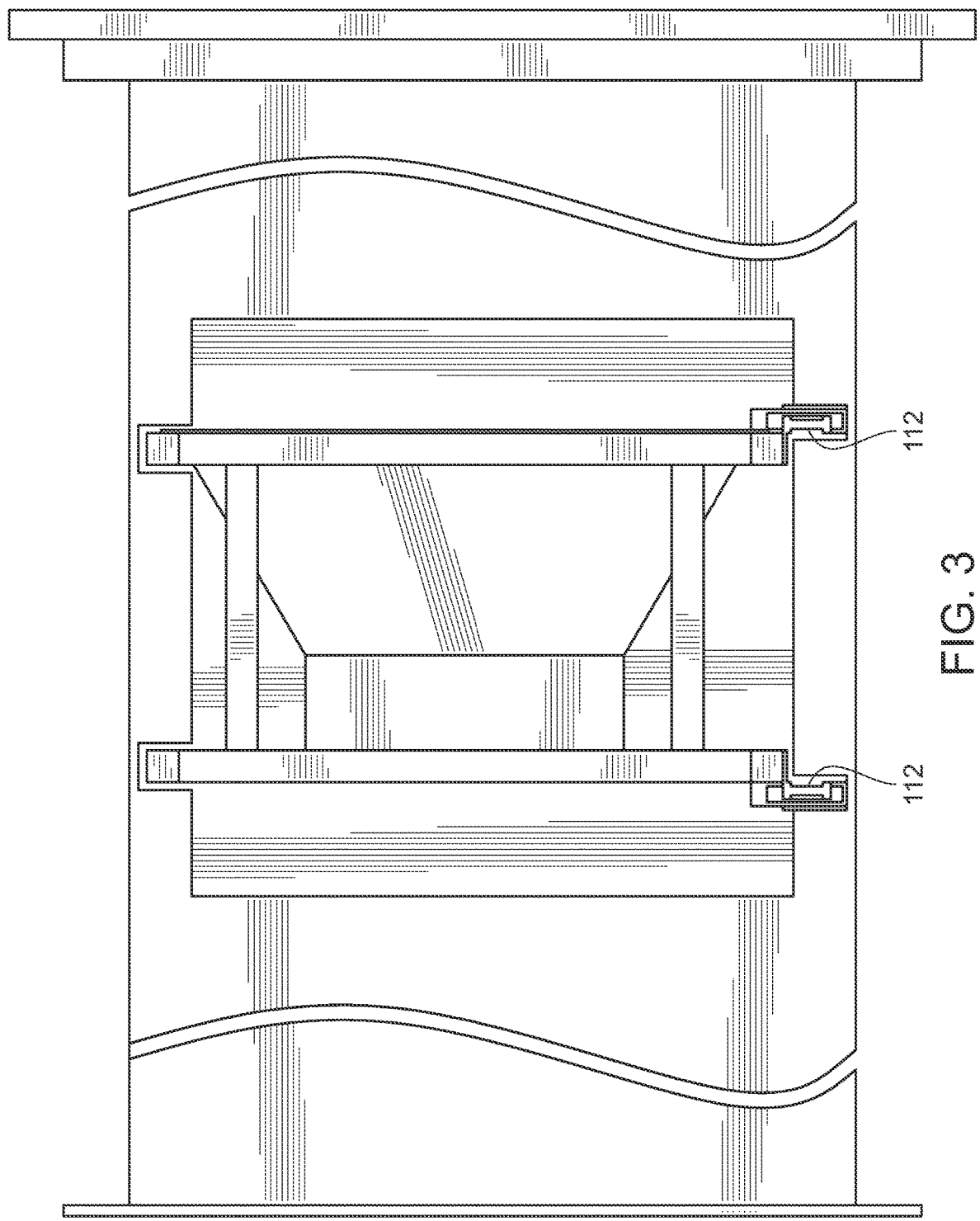
FIG. 3 is a side perspective viewing, showing an example embodiment of the energy recapturing apparatus and the fluid passageway according to the present disclosure.

In preferred embodiments, the frame 110 is disposed upon a sliding mechanism 112 such that the sliding mechanism 112 is disposed on an exterior of the frame 110. Preferably, the sliding mechanism 112 is configured to support the weight of the frame 110 and at least one turbine 120. Also, preferably, the sliding mechanism 112 is comprised of one or more slide rails. In many embodiments each slide rail is rated to support up to 250 pounds of weight. In preferred embodiments, one slide rail is attached to the front end 110A of the bottom side 110F and a second slide rail is attached to the rear end 110B of the bottom side 110F. However, in alternative embodiments, the sliding mechanism 112 is attached to any one of the left side 110C, the right side 110D, the top side 110E, or the bottom side 110F. In an embodiment, with reference to FIG. 3 and FIG. 4, the sliding mechanism 112 has both an extended mode and a non-extended mode. In a preferred embodiment, the sliding mechanism is configured so that the frame is situated within the fluid passageway when the sliding mechanism is in the non-extended mode. In a preferred embodiment, the sliding mechanism is configured so that the frame is partially or completely removed from the fluid passageway when the sliding mechanism is in the extended mode.

Alternatively, the sliding mechanism 112 may be connected to any one or a combination of the left side 110C, the right side 110D, the top side 110E, or the bottom side 110F. In further embodiments, the sliding mechanism 112 has two or more slide rails.

In alternate embodiments, the frame 110 is connected to multiple sliding mechanisms. Such an embodiment may have one sliding mechanism attached to the top side 110E and a second sliding mechanism attached to the bottom side 110F. However, any number of sliding mechanisms may be attached to any number or combination of sides 110C, 110D, 110E, and 110D.

In preferable embodiments the sliding mechanism 112 enables the entire frame 110 to be removed from the preexisting fluid passageway. However, there are other embodiments that may only allow part of the frame 110 to be removed from the preexisting fluid passageway due to spatial or weight limitations.

In an exemplary embodiment, the frame 110 exterior is fitted with a seal such that when the frame 110 is disposed into the preexisting fluid passageway the seal prevents fluid from escaping. The seal is preferably made from rubber but may be composed of other materials. In another exemplary embodiment, the interior of the continuous sheet 110G is fitted with soundproofing material. Alternatively, the exterior of the frame 110 may be fitted with soundproofing material. The soundproofing material may be composed of a foam or other material known in the arts to dampen sound.

In preferred embodiments, the at least one turbine 120 is attached to the at least one mounting bracket 114. The at least one turbine 120 may be attached to the at least one bracket 114 with screw, nuts and bolts, weld, adhesive, or other means of fastening. Preferably, the at least one turbine 120 is disposed at the center of the preexisting fluid passageway. Also preferably, the at least one turbine 120 comprises a plurality of blades 122, a rotor 124, a nacelle 126, and a generator 128. The plurality of blades 122 may be comprised of a number of blades that, preferably, each extend radially from the rotor 124, such that the plurality of blades 122 are perpendicular or roughly perpendicular to the fluid flowing through the preexisting fluid passageway. However, there are alternate embodiments where each of the plurality of blades 122 extend radially and outward from the rotor.

Preferably each of the plurality of blades 122 are spaced equally from each other. Also preferably, each of the plurality of blades 122 contains 11 blades. However, in alternate embodiments the plurality of blades 122 may contain any number of blades. In alternative embodiments, either the rotor 124, the at least one turbine 120, the plurality of blades 122, the at least one mounting bracket 114, or the frame 110, may be angled such that the plurality of blades 122 are facing the incoming fluid at a non-perpendicular angle. In this embodiment, the plurality of blades 122 would not be exactly perpendicular to the incoming fluid. Further, in this embodiment, the angle of the plurality of blades 122 in relation to the incoming fluid may be adjustable.

Further, a mesh screen or other filter may be disposed upon the frame such that the mesh screen or other filters completely or partially covers the passage 110H. Such a mesh screen or other filter may act to obstruct particles or debris that would otherwise damage the at least one turbine 120.

Alternatively, the energy recapturing apparatus may contain more that one plurality of blades. In such an embodiment, the more than one plurality of blades may be disposed such that one plurality of blades is behind the other. Preferably, in such an embodiment, each plurality of blades would be oriented at the same angle. However, there are further alternate embodiments that may benefit from more that one plurality blades such that each plurality of blades is situated at different angles.

In preferred embodiments, the generator 128 has an electrical output cable 128A that is configured to carry electricity. Preferably the electrical output cable 128A is connected to a battery bank. However, the electrical output cable 128A may be connected directly to an appliance, other device that is powered by electricity, or directly or indirectly to the electrical grid of the building.

In an alternate embodiment, the nacelle 126 completely surrounds the plurality of blades 122, the rotor 124, the generator 128, and the shaft 130. Preferably, this embodiment of the energy recapturing apparatus may contain a duct or cone that directs the fluid or air straight into the at least one turbine 120. In this embodiment, the duct or cone that directs air into the at least one turbine 120 may be attached to the front end 110A of the frame 110. Alternatively, the duct or cone that directs air into the at least one turbine 120 may be comprised of the nacelle 126 itself. In such an embodiment, the nacelle 126 may extend into the oncoming fluid or air such that this extension of the nacelle 126 tapers towards the plurality of blades 122. Also, preferably, the plurality of blades 122 are attached to the rotor 124 which is further attached to a shaft 130. The shaft 130 may be permanently attached to the rotor 124. The shaft 130 may be further attached to the generator 128.

In a preferred embodiment, the at least one turbine further comprises a brake that stops the rotation of the plurality of blades 122. Such a brake may be invoked when the incoming fluid or air reaches more than 150 miles per hour. However, in other embodiments, the brake may be set to different speed thresholds. In this embodiment, the at least one turbine further comprises a controller that may start the at least one turbine at certain air speeds or initiate the brake at certain speed thresholds.

In other embodiments the at least one turbine 120 further comprises a gear box and a high-speed shaft. Preferably, the gear box is disposed between the shaft 130 and high-speed shaft. In preferable embodiments, the gear box contains one or more gears that are configured to increase rotational speed. In this embodiment, the high-speed shaft is further attached to the generator 128.

In alternate embodiments, there are two or more turbines 120 attached to at least one, but preferably more, mounting brackets 114. In such an alternate embodiment, the frame 110 supports two or more turbines 120. Preferably, the two or more turbines 120 are evenly spaced across the frame 110.

In a preferred embodiment, the at least one turbine 120 can be inserted in a subframe 200. In some embodiments the subframe 200 is integrated into the frame 110. In other embodiments, each of a plurality of turbines 120 can each be inserted into each of a plurality of subframes 200. In those embodiments, the plurality of subframes 200 can be integrated together creating a conglomerate of subframes 202. In an exemplary embodiment, the at least one turbine 120 combined with the subframe 200 is the MicroCube®, sold by American Wind, more thoroughly described in U.S. Pat. No. 9,331,534, the contents of which are hereby incorporated by reference in their entirety.

In a preferred embodiment, the subframe 200 may be attached to the at least one mounting bracket 114. In an exemplary embodiment, the conglomerate of subframes 202 are attached to the at least one mounting bracket 114.

An embodiment of the energy recapturing apparatus of the present invention, with reference to FIG. 5A-F, also includes at least one turbine collar 140. In some embodiments, the energy recapturing apparatus of the present inventions includes a plurality of turbine collars 140. In an embodiment, each turbine collar 140 has a first end 142 with a first size 144, the first size 144 having a first length 144A and a first width 144B, and a second end 146 with a second size 148, the second size 148 having a second length 148A and a second width 148B. In an embodiment, the first size 144 of the at least one turbine collar 140 is sized to a cross section of the at least one turbine and the first end 142 is in fluid communication with the at least one turbine 120. In an embodiment, the second size 148 is sized to a cross section of the fluid passageway. In some embodiments, the first size 144 and second size 148 of each of the at least one turbine collar 120 are all the same. In other embodiments, at least one of the turbine collars 120 has a first size 144 and/or a second size 148 that is different from the rest of the turbine collars 120. In an embodiment, the second size 148 is larger than the first size 144.

In an embodiment, the energy recapturing apparatus includes a plurality of turbines 120, and the first size 144 is sized to a combined cross section of the plurality of turbines and the first end 142 is in fluid communication with the plurality of turbines 120. In some embodiments, the first width 144A and the first length 144B are the same. In other embodiments, the first width 144A and the first length 144B are different. In some embodiments, there are a plurality of turbines 120, and the first width 144A is sized such that it matches the width or length of one of the plurality of turbines 120, and the first length 144B is sized such that it matches the combined width or length of two or more of the plurality of turbines 120. In some embodiments, there are a plurality of turbines 120 and a plurality of turbine collars 140, preferably such that each turbine 120 is in fluid communication with at least one turbine collar 140. In some embodiments, the combined second width 148A and the combined second length 148B of the plurality of turbine collars is sized to a cross section of the fluid passageway.

In an embodiment, the fluid passageway is a return air duct. In an embodiment, the fluid passageway is a building air intake. It is understood by persons skilled in the art that the fluid passageway may be any passageway in a building through which air is moved by climate control machinery or apparatuses or through other means as part of the normal functioning of the building.

In an embodiment, the energy recapturing apparatus generates at least 500 Watts of energy when situated in the fluid passageway. In an embodiment, the energy recapturing apparatus generates at least 1000 Watts of energy when situated in the fluid passageway. In an embodiment, the energy recapturing apparatus generates at least 1500 Watts of energy when situated in the fluid passageway. In an embodiment, the energy recapturing apparatus generates at least 3000 Watts of energy when situated in the fluid passageway. In an embodiment, the energy recapturing apparatus generates between 500 and 15000 Watts of energy when situated in the fluid passageway, preferably between 500 and 10000 Watts, more preferably between 500 and 5000 Watts of energy. In some embodiments, the energy recapturing apparatus generates between 1 kiloWatt and 100 kiloWatts of energy when situated in the fluid passageway. It is understood that the amount of energy generated by the energy recapturing apparatus depends on many factors, such as the rate of air flow through the fluid passageway, the number of turbines situated within the energy recapturing apparatus, the static pressure of the system, and others.

It is understood that when an element is referred hereinabove as being "on" another element, it can be directly on the other element or intervening elements may be present therebetween. In contrast, when an element is referred to as being "directly on" another element, there are no intervening elements present.

Moreover, any components or materials can be formed from a same, structurally continuous piece or separately fabricated and connected.

It is further understood that, although ordinal terms, such as, "first," "second," and "third," are used herein to describe various elements, components, regions, layers and/or sections, these elements, components, regions, layers and/or sections should not be limited by these terms. These terms are only used to distinguish one element, component, region, layer and/or section from another element, component, region, layer and/or section. Thus, a "first element," "component," "region," "layer" and/or "section" discussed below could be termed a second element, component, region, layer and/or section without departing from the teachings herein.

Features illustrated or described as part of one embodiment can be used with another embodiment and such variations come within the scope of the appended claims and their equivalents.

Spatially relative terms, such as "beneath," "below," "lower," "above," "upper" and the like, are used herein for ease of description to describe one element or feature's relationship to another element(s) or feature(s) as illustrated in the figures. It is understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device can be otherwise oriented (rotated 90 degrees or at other orientations) and the spatially relative descriptors used herein interpreted accordingly.

Example embodiments are described herein with reference to cross section illustrations that are schematic illustrations of idealized embodiments. As such, variations from the shapes of the illustrations, for example, of manufacturing techniques and/or tolerances, are to be expected. Thus, example embodiments described herein should not be construed as limited to the particular shapes of regions as illustrated herein, but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

As the invention has been described in connection with what is presently considered to be the most practical and various embodiments, it is to be understood that the invention is not to be limited to the disclosed embodiments, but on the contrary, is intended to cover various modifications and equivalent arrangements included within the scope of the appended claims. Although specific terms are employed herein, they are used in a generic and descriptive sense only and not for purposes of limitation.

This written description uses examples to disclose the invention, including the best mode, and also to enable any person skilled in the art to practice the invention, including making and using any devices or systems and performing any incorporated methods. The patentable scope of the invention is defined in the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

In conclusion, herein is presented an energy recapturing apparatus. The disclosure is illustrated by example in the drawing figures, and throughout the written description. It should be understood that numerous variations are possible while adhering to the inventive concept. Such variations are contemplated as being a part of the present disclosure.

EXAMPLE 1

Figure 4:
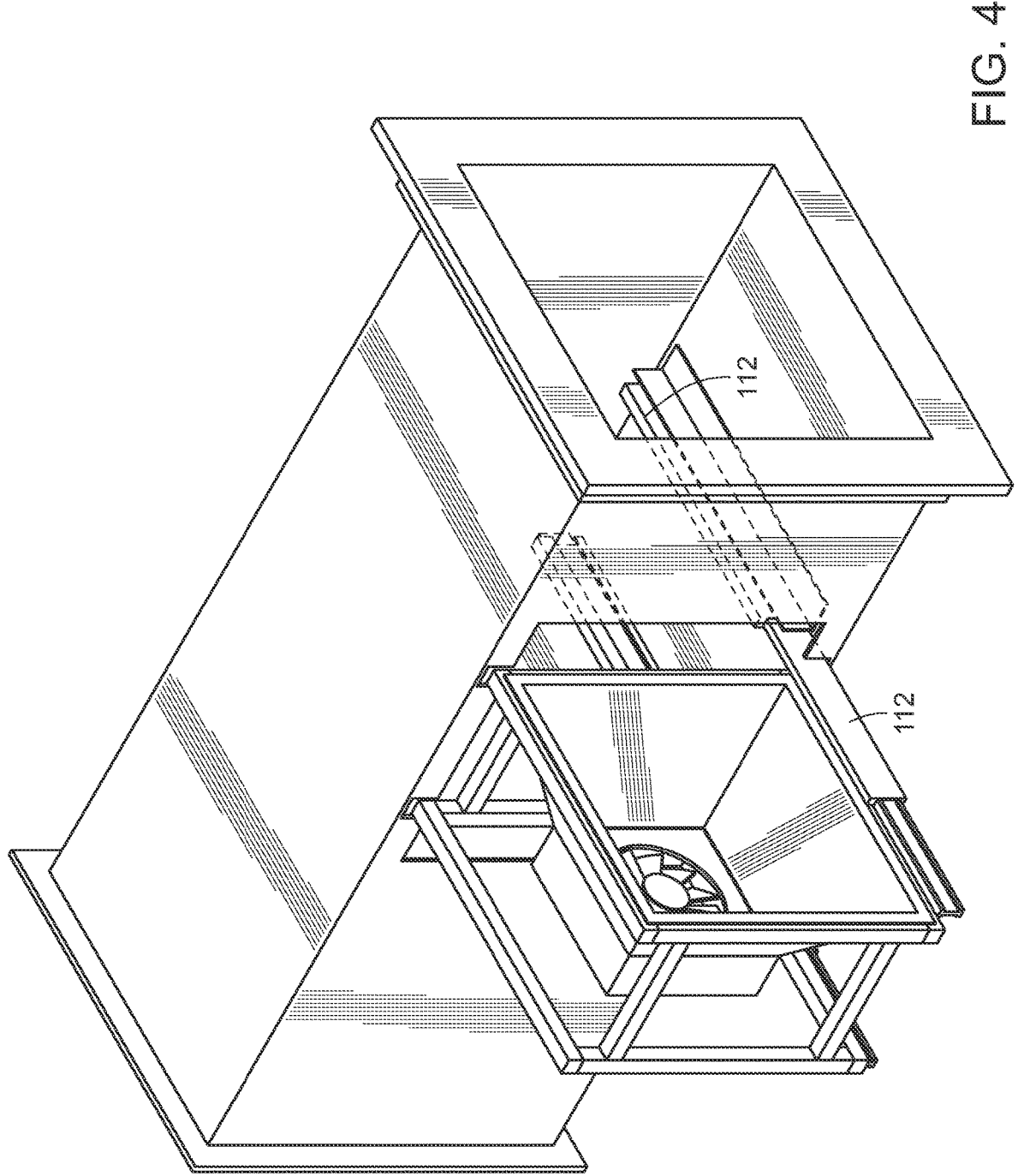
FIG. 4 is a front perspective viewing, showing an alternate example embodiment of the energy recapturing apparatus and the fluid passageway according to the present disclosure.
Figures 5A, 5D:
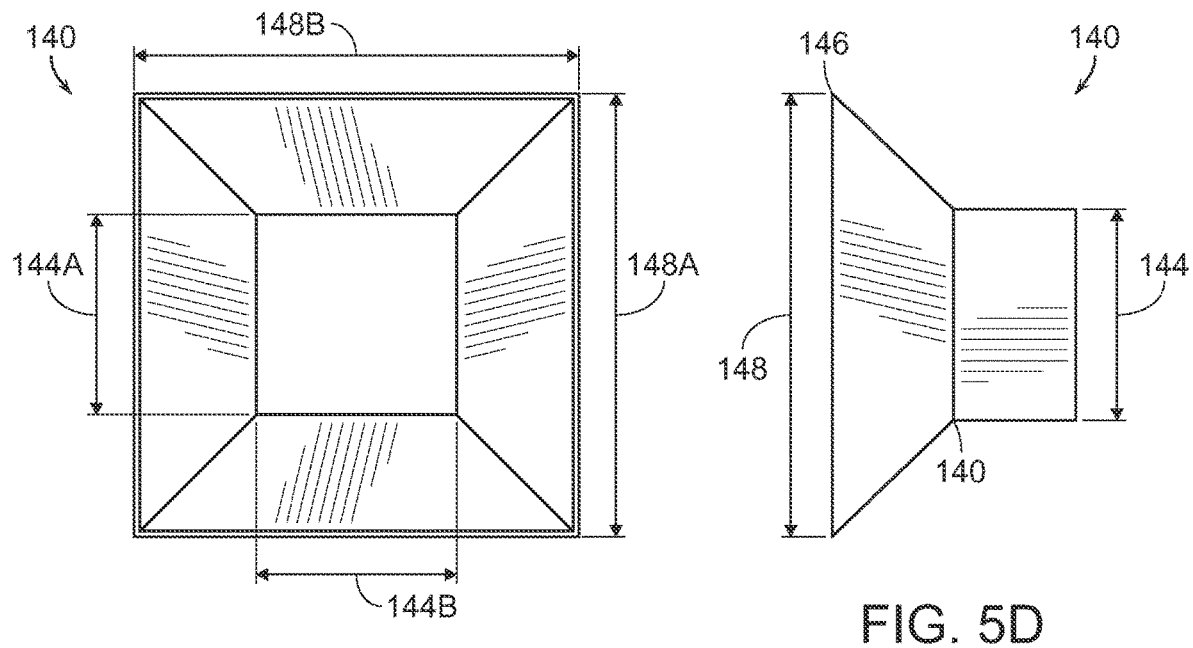
FIGS. 5A-5C are front perspective viewings, showing example embodiments of the turbine collar according to the present disclosure.
FIGS. 5D-5F are side perspective viewings, showing example embodiments of the turbine collar according to the present disclosure.
Figures 5B, 5E:
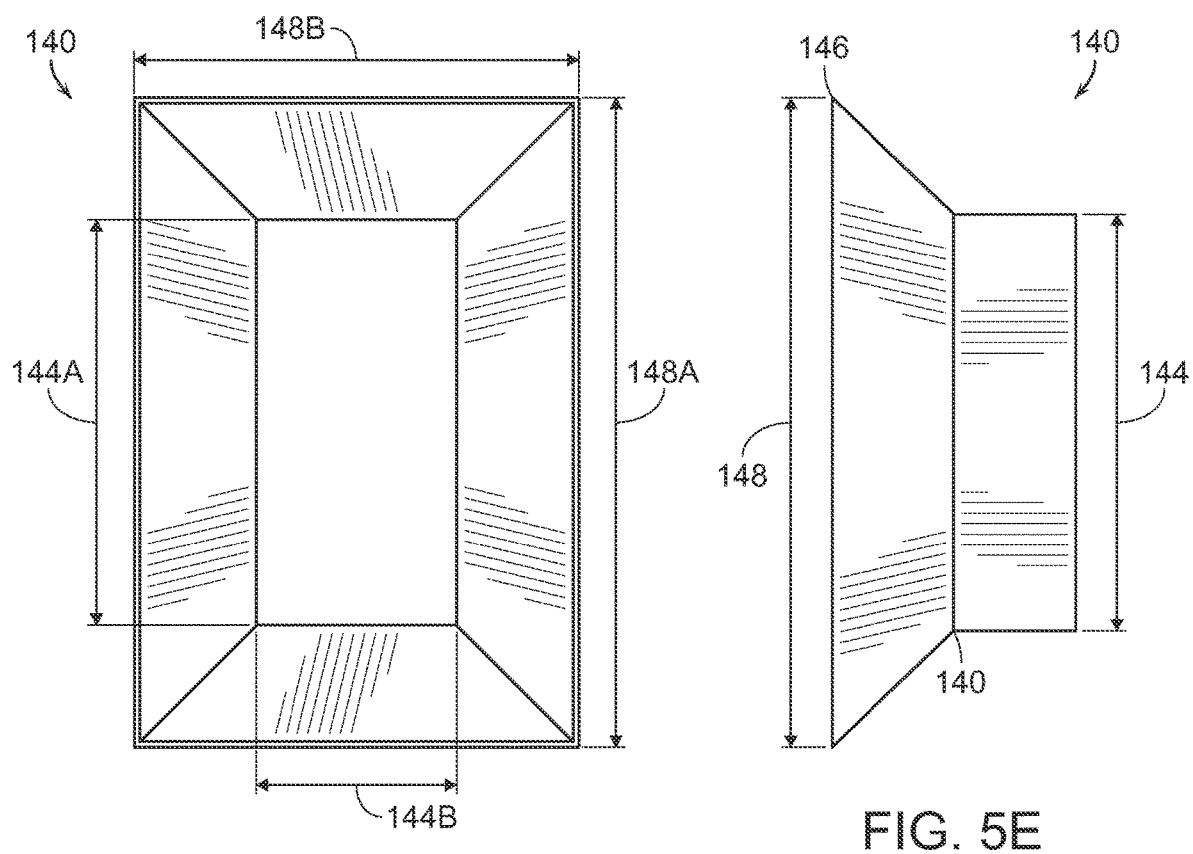
Figures 5C, 5F:
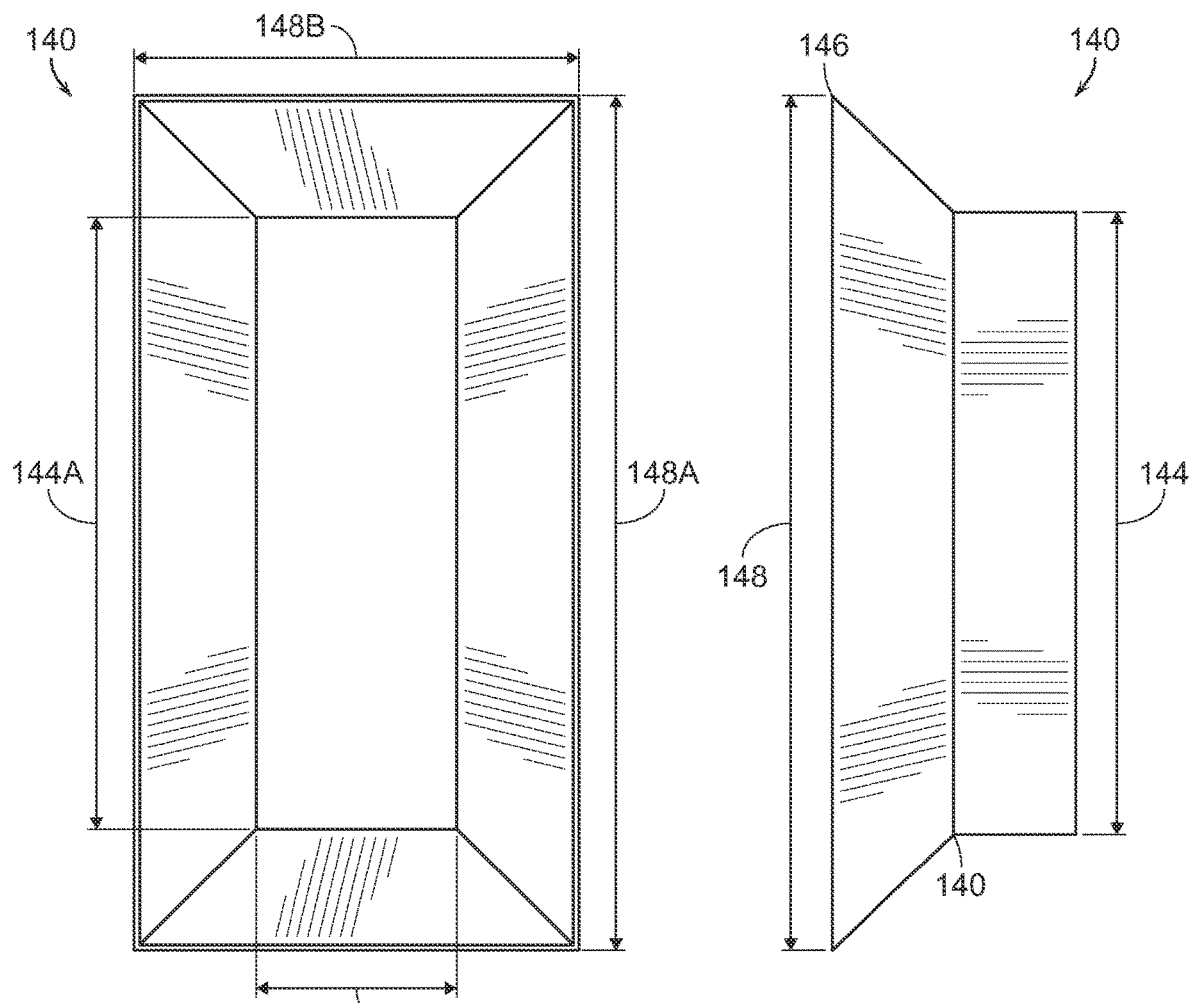

An example apparatus of the present invention, with reference to the embodiments disclosed in FIG. 2 and FIG. 4, was constructed. The example apparatus included a total of six American Wind MicroCubes®, arranged in two linear rows of three American Wind MicroCubes® each. Each row had a width equivalent to the length of the side of one turbine, and a length equivalent to the combined lengths of the sides of three turbines. The example apparatus further included two turbine collars made according to the present disclosure, with each turbine collar sized and attached to a row of MicroCubes®.

The rows of turbines and attached turbine collars were mounted, side by side such that the longitudinal axes of the rows were parallel, on a frame sized to the fluid passageway, with attached slide rails, made according to the present disclosure. The turbines were in electronic communication, and configured such that they were connected electrically in series.

The example apparatus was mounted inside a 28" by 33" intake duct for a 10 ton air handler unit, inside a test building. Such intake duct had approximately 7,500 cubic feet per minute (CFM) of air flow moving through it.

The example apparatus was set to run for six days, and the voltage and energy generation data from the example apparatus was collected. The data collected from the example apparatus is shown in the table below:

TABLE 1

| Date | Time | DC voltage of six turbines connected in series | AC Voltage (DC/.636) | Watts from six turbines connected in series, at approximately 4.75 amps. (Volts × Amps) (±.05) |
|---|---|---|---|---|
| May 24, 2021 | 2:50 PM | 455 | 715 | 3,396 Watts |
| May 24, 2021 | 7:10 PM | 465 | 731 | 3,472 Watts |
| May 25, 2021 | 8:05 AM | 450 | 707 | 3,358 Watts |
| May 25, 2021 | 12:15 PM | 458 | 720 | 3,420 Watts |
| May 25, 2021 | 6:00 PM | 460 | 723 | 3,434 Watts |
| May 26, 2021 | 8:00 AM | 466 | 732 | 3,477 Watts |
| May 26, 2021 | 1:35 PM | 462 | 726 | 3,448 Watts |
| May 26, 2021 | 7:00 PM | 470 | 739 | 3,510 Watts |
| May 27, 2021 | 7:45 AM | 470 | 739 | 3,510 Watts |
| May 27, 2021 | 1:00 PM | 475 | 747 | 3,548 Watts |
| May 27, 2021 | 7:15 PM | 465 | 731 | 3,472 Watts |
| May 28, 2021 | 8:00 AM | 472 | 742 | 3,524 Watts |
| May 28, 2021 | 3:30 PM | 470 | 739 | 3,510 Watts |
| May 28, 2021 | 8:30 PM | 464 | 730 | 3,467 Watts |
| May 29, 2021 | 7:40 AM | 471 | 741 | 3,520 Watts |
| May 29, 2021 | 3:30 PM | 475 | 747 | 3,548 Watts |

The data collected from the example apparatus indicated that the example apparatus was able to recapture a consistent amount of energy, between 3300 and 3600 Watts, from the air flow within the intake duct, under the provided conditions.

EXAMPLE 2

An example apparatus of the present invention, with reference to the embodiments disclosed in FIG. 2 and FIG. 4, was constructed. The example apparatus included a single American Wind MicroCube®, with a single turbine collar made according to the present disclosure attached to the turbine. The turbine and turbine collar were mounted on a frame, with attached slide rails, made according to the present disclosure.

The example apparatus was mounted inside a 12" by 12" branch line duct of a large package unit, inside of a test building. Such branch line duct had approximately 1,500 CFM of air flow moving through it.

The example apparatus was set to run for three days, and the voltage and energy generation data from the example apparatus was collected. The data collected from the example apparatus is shown in the table below:

TABLE 2

| Date | Time | DC voltage of one turbine | AC Voltage (DC/.636) | Watts from one turbine, at approximate. 4.95 amps (Volts × Amps) (±.05) |
|---|---|---|---|---|
| May 12, 2021 | 8:00 AM | 85 | 134 | 663 Watts |
| May 12, 2021 | 12:00 PM | 85 | 134 | 663 Watts |

TABLE 2-continued

| Date | Time | DC voltage of one turbine | AC Voltage (DC/.636) | Watts from one turbine, at approximate. 4.95 amps (Volts × Amps) (±.05) |
|---|---|---|---|---|
| May 12, 2021 | 8:30 PM | 88 | 138 | 683 Watts |
| May 13, 2021 | 7:30 AM | 86 | 135 | 663 Watts |
| May 13, 2021 | 12:00 PM | 85 | 134 | 663 Watts |
| May 13, 2021 | 8:00 PM | 88 | 138 | 683 Watts |
| May 14, 2021 | 7:40 AM | 90 | 142 | 703 Watts |
| May 14, 2021 | 1:00 PM | 86 | 135 | 663 Watts |
| May 14, 2021 | 7:30 PM | 90 | 142 | 703 Watts |

The data collected from the example apparatus indicated that the example apparatus was able to recapture a consistent amount of energy, between 650 and 750 Watts, from the air flow within the branch line duct, under the provided conditions.

EXAMPLE 3

An example apparatus of the present invention, with reference to the embodiments disclosed in FIG. 2 and FIG. 4, was constructed. The example apparatus included two American Wind MicroCubes® arranged in a row, with a single turbine collar made according to the present disclosure attached to the two turbines. The turbines and turbine collar were mounted on a frame, with attached slide rails, made according to the present disclosure. The turbines were in electronic communication, and configured such that they were connected electrically in series.

The example apparatus was mounted inside a 24" by 18" return air duct, inside of a test building. This return air duct was feeding to a 7.5 ton air handler unit. Such return air duct had approximately 3,000 CFM of air flow moving through it.

The example apparatus was set to run for ten days, and the voltage and energy generation data from the example apparatus was collected. The data collected from the example apparatus is shown in the table below:

| Date | Time | DC voltage Turbine 1 | DC voltage Turbine 2 | AC Voltage (DC/.636) | Watts from both turbines connected in series. (Volts × Amps) (±.05) |
|---|---|---|---|---|---|
| Jun. 1, 2021 | 10:00 AM | 91 | 91 | 143 | 1,458 Watts |
| Jun. 1, 2021 | 6:50 PM | 93 | 91 | 146/143 | 1,474 Watts |
| Jun. 2, 2021 | 8:00 AM | 91 | 91 | 143 | 1,458 Watts |
| Jun. 2, 2021 | 2:35 PM | 90 | 93 | 141/146 | 1,463 Watts |
| Jun. 2, 2021 | 7:10 PM | 89 | 90 | 140/141 | 1,433 Watts |
| Jun. 3, 2021 | 7:35 AM | 92 | 90 | 144/141 | 1,453 Watts |
| Jun. 3, 2021 | 12:15 PM | 91 | 92 | 143/144 | 1,463 Watts |
| Jun. 3, 2021 | 9:05 PM | 94 | 94 | 148 | 1,509 Watts |
| Jun. 4, 2021 | 8:10 AM | 96 | 94 | 151/148 | 1,525 Watts |
| Jun. 4, 2021 | 1:05 PM | 93 | 94 | 146/148 | 1,499 Watts |
| Jun. 4, 2021 | 6:35 PM | 95 | 93 | 149/146 | 1,504 Watts |
| Jun. 5, 2021 | 8:25 PM | 96 | 95 | 151/149 | 1,530 Watts |
| Jun. 5, 2021 | 3:50 PM | 92 | 90 | 143/141 | 1,448 Watts |
| Jun. 6, 2021 | 8:00 AM | 95 | 96 | 143/151 | 1,530 Watts |
| Jun. 6, 2021 | 3:30 PM | 96 | 98 | 151/154 | 1,555 Watts |
| Jun. 7, 2021 | 8:05 AM | 93 | 95 | 146/149 | 1,504 Watts |
| Jun. 7, 2021 | 1:05 PM | 92 | 95 | 144/149 | 1,494 Watts |
| Jun. 7, 2021 | 8:10 PM | 96 | 93 | 151/146 | 1,515 Watts |
| Jun. 8, 2021 | 8:00 AM | 92 | 97 | 144/153 | 1,514 Watts |
| Jun. 8, 2021 | 12:300 PM | 91 | 92 | 143/144 | 1,463 Watts |
| Jun. 8, 2021 | 8:35 PM | 95 | 96 | 143/151 | 1,530 Watts |
| Jun. 9, 2021 | 8:00 AM | 95 | 95 | 146/146 | 1,489 Watts |

| Date | Time | DC voltage Turbine 1 | DC voltage Turbine 2 | AC Voltage (DC/.636) | Watts from both turbines connected in series. (Volts × Amps) (±.05) |
|---|---|---|---|---|---|
| Jun. 9, 2021 | 1:30 PM | 98 | 96 | 154/151 | 1,551 Watts |
| Jun. 9, 2021 | 8:05 PM | 93 | 95 | 146/149 | 1,504 Watts |
| Jun. 10, 2021 | 7:45 AM | 96 | 96 | 143/151 | 1,499 Watts |

The data collected from the example apparatus indicated that the example apparatus was able to recapture a consistent amount of energy, between 1400 and 1600 Watts, from the air flow within the return air duct, under the provided conditions.

EXAMPLE 4

An example apparatus of the present invention, with reference to the embodiments disclosed in FIG. 2 and FIG. 4, was constructed. The example apparatus included a total of six American Wind MicroCubes®, arranged in two linear rows of three American Wind MicroCubes® each. Each row had a width equivalent to the length of the side of one turbine, and a length equivalent to the combined lengths of the sides of three turbines. The example apparatus further included two turbine collars made according to the present disclosure, with each turbine collar sized and attached to a row of MicroCubes®.

The rows of turbines and attached turbine collars were mounted, end-to-end, such that the longitudinal axes of the rows were aligned to form a single line, on a frame sized to the fluid passageway, with attached slide rails, made according to the present disclosure. The turbines were in electronic communication, and configured such that they were connected electrically in series.

The example apparatus was mounted inside a 14" by 84" intake duct for a 15 ton chiller unit, inside a test building. Such intake duct had approximately 6,000 cubic feet per minute (CFM) of air flow moving through it.

The example apparatus was set to run for seven days, and the voltage and energy generation data from the example apparatus was collected. The data collected from the example apparatus is shown in the table below:

TABLE 4

| Date | Time | DC voltage of six turbines connected in series | AC Voltage (DC/.636) | Watts from six turbines connected in series, at approximately 4.9 amps. (Volts × Amps) (±.05) |
|---|---|---|---|---|
| Jun. 22, 2021 | 8:30 AM | 495 | 778 | 3,812 Watts |
| Jun. 22, 2021 | 12:00 PM | 495 | 778 | 3,812 Watts |
| Jun. 22, 2021 | 7:30 PM | 492 | 774 | 3,793 Watts |
| Jun. 23, 2021 | 8:00 AM | 498 | 783 | 3,837 Watts |
| Jun. 23, 2021 | 12:15 PM | 500 | 786 | 3,851 Watts |
| Jun. 23, 2021 | 8:45 PM | 500 | 786 | 3,851 Watts |
| Jun. 24, 2021 | 8:10 AM | 495 | 778 | 3,812 Watts |
| Jun. 24, 2021 | 1:05 PM | 503 | 791 | 3,876 Watts |
| Jun. 24, 2021 | 6:35 PM | 505 | 794 | 3,891 Watts |
| Jun. 25, 2021 | 8:00 AM | 498 | 783 | 3,837 Watts |
| Jun. 25, 2021 | 2:00 PM | 500 | 786 | 3,851 Watts |
| Jun. 25, 2021 | 7:00 PM | 505 | 794 | 3,891 Watts |
| Jun. 26, 2021 | 7:30 AM | 498 | 783 | 3,837 Watts |
| Jun. 26, 2021 | 3:30 PM | 500 | 786 | 3,851 Watts |
| Jun. 27, 2021 | 7:15 AM | 501 | 788 | 3,861 Watts |
| Jun. 27, 2021 | 3:30 PM | 500 | 786 | 3,851 Watts |
| Jun. 28, 2021 | 9:00 AM | 499 | 785 | 3,846 Watts |

The data collected from the example apparatus indicated that the example apparatus was able to recapture a consistent amount of energy, between 3700 and 4000 Watts, from the air flow within the return air duct, under the provided conditions.

What is claimed is:

1. An energy recapturing apparatus for use with a preexisting fluid passageway, comprising:
    a frame having a left side, a right side, a top side, and a bottom side, having a front end and a rear end, the frame sized to be removably inserted within a cross section of the fluid passageway;
    at least one turbine having a front end and a back end, wherein the at least one turbine comprising a mounting mechanism for attachment to the frame,
        wherein the frame and the at least one turbine are oriented such that air passing through the cross section will also pass through the energy recapturing apparatus; and
    a sliding mechanism disposed on an exterior of the frame and connected to the preexisting fluid passageway, having an extended mode and a non-extended mode,
        wherein the sliding mechanism is configured to support the frame and the at least one turbine,
        wherein the sliding mechanism is further configured to enable the frame to be situated within the fluid passageway when the sliding mechanism is in the non-extended mode, and
        wherein the frame and turbine are configured to be removably attached to the fluid passageway when the sliding mechanism is in the extended mode.

2. The energy recapturing apparatus of claim 1, further comprising at least one turbine collar, each turbine collar having a first end with a first size, the first size being defined by a first length and a first width, a second end with a second size, the second size being defined by a second length and width, and at least one wall extending therebetween, the at least one turbine collar being affixed to the at least one turbine.

3. The energy recapturing apparatus of claim 2, wherein the first size is sized to a cross section of the at least one turbine and the first end is in fluid communication with the at least one turbine.

4. The energy recapturing apparatus of claim 2, wherein the at least one turbine is a plurality of turbines and wherein the first size is sized to a combined cross section of the plurality of turbines and the first end is in fluid communication with the plurality of turbines.

5. The energy recapturing apparatus of claim 2, wherein the at least one turbine is at least two turbines, wherein the first width is sized to a length of a side of a turbine and the first length is sized to a combined length of a side of each of the at least two turbines, and wherein the first end is in fluid communication with the at least two turbines.

6. The energy recapturing apparatus of claim 2, wherein the at least one turbine is a plurality of turbines, wherein the at least one turbine collar is a plurality of turbine collars, and wherein at least one of the plurality of turbines is in fluid communication with at least one of the plurality of turbine collars.

7. The energy recapturing apparatus of claim 6, wherein the first width of each of the plurality of turbine collars is sized to a length of a side of a turbine and the first length of each of the plurality of turbine collars is sized to a combined length of a side of each of at least two turbines of the plurality of turbines, and wherein the first end of each of the plurality of turbine collars is in fluid communication with at least two turbines of the plurality of turbines.

8. The energy recapturing apparatus of claim 2, wherein the second size is defined by a cross section of the fluid passageway.

9. The energy recapturing apparatus of claim 6, wherein the combined second width and combined second length of the plurality of turbine collars is sized to a cross section of the fluid passageway.

10. The energy recapturing apparatus of claim 2, wherein the second size is larger than the first size.

11. The energy recapturing apparatus of claim 8, wherein the fluid passageway is a return air duct.

12. The energy recapturing apparatus of claim 8, wherein the fluid passageway is a building air intake.

13. The energy recapturing apparatus of claim 8, wherein the fluid passageway is a branch line duct.

14. The energy recapturing apparatus of claim 9, wherein the fluid passageway is a return air duct.

15. The energy recapturing apparatus of claim 9, wherein the fluid passageway is a building air intake.

16. The energy recapturing apparatus of claim 11, wherein the energy recapturing apparatus generates at least 1000 Watts of energy.

17. The energy recapturing apparatus of claim 11, wherein the energy recapturing apparatus generates at least 1500 Watts of energy.

18. The energy recapturing apparatus of claim 12, wherein the energy recapturing apparatus generates at least 3000 Watts of energy.

19. The energy recapturing apparatus of claim 14, wherein the energy recapturing apparatus generates at least 3000 Watts of energy.

20. The energy recapturing apparatus of claim 2, wherein the energy recapturing apparatus generates between 500 and 10,000 Watts of energy.

* * * * *